United States Patent
Kumbhani et al.

(10) Patent No.: US 9,663,456 B2
(45) Date of Patent: May 30, 2017

(54) INTERMEDIATE OF TAPENTADOL

(71) Applicant: SUN PHARMA ADVANCED RESEARCH COMPANY, Maharashtra (IN)

(72) Inventors: Anil Kumbhani, Baroda (IN); Biswajit Samanta, Baroda (IN); Kilaru Srinivasu, Baroda (IN); Thennati Rajamannar, Baroda (IN)

(73) Assignee: SUN PHARMA ADVANCED RESEARCH COMPANY, Mumbai Maharashtra (IN)

( * ) Notice: Subject to any disclaimer, the term of this patent is extended or adjusted under 35 U.S.C. 154(b) by 0 days.

(21) Appl. No.: 15/033,331

(22) PCT Filed: Oct. 31, 2014

(86) PCT No.: PCT/IN2014/000696
§ 371 (c)(1),
(2) Date: Apr. 29, 2016

(87) PCT Pub. No.: WO2015/075744
PCT Pub. Date: May 28, 2015

(65) Prior Publication Data
US 2016/0264521 A1    Sep. 15, 2016

(30) Foreign Application Priority Data
Nov. 1, 2013   (IN) .......................... 3478/MUM/2013

(51) Int. Cl.
| | | |
|---|---|---|
| *C07C 271/00* | (2006.01) | |
| *C07C 271/28* | (2006.01) | |
| *C07C 269/02* | (2006.01) | |
| *C07C 213/08* | (2006.01) | |

(52) U.S. Cl.
CPC .......... *C07C 271/28* (2013.01); *C07C 213/08* (2013.01); *C07C 269/02* (2013.01)

(58) Field of Classification Search
CPC ... C07C 213/08; C07C 271/28; C07C 269/02; C07C 215/54; C07C 217/62
See application file for complete search history.

(56) References Cited

FOREIGN PATENT DOCUMENTS

| EP | 0693475 A1 | 1/1996 |
|---|---|---|
| WO | 2008012046 A1 | 1/2008 |
| WO | WO2008/012046 | * 1/2008 |

OTHER PUBLICATIONS

Ma, Yanquin et al. "Synthesis of tapentadol hydrochloride" Zhongguo Yiyao Gongye Zazhi (2013), 44(6), 554-556; ISSN: 1001-8255 (Abstract), CAPLUS [online] Copyright 2015 ACS on STN (retrieved on Jun. 5, 2015], Retrieved from STN International, Karlsruhe, Accession No. 2013:1967227 CAPLUS. Abstract.
International Search Report filed Oct. 31, 2014.

* cited by examiner

*Primary Examiner* — Yevegeny Valenrod
*Assistant Examiner* — Blaine G Doletski
(74) *Attorney, Agent, or Firm* — Sughrue Mion, PLLC

(57) ABSTRACT

The present invention relates to novel carbamate intermediate of formula (II), process for its preparation and process for its conversion into 3-[(1R,2R)-3-(dimethylamino)-1-ethyl-2-methylpropyl]phenol, tapentadol and its pharmaceutically acceptable salts.

10 Claims, No Drawings

INTERMEDIATE OF TAPENTADOL

FIELD OF INVENTION

The present invention relates to novel intermediate of Formula II, process for its preparation and process for its conversion into 3-[(1R,2R)-3-(dimethylamino)-1-ethyl-2-methylpropyl]phenol, tapentadol of Formula I and its pharmaceutically acceptable salts.

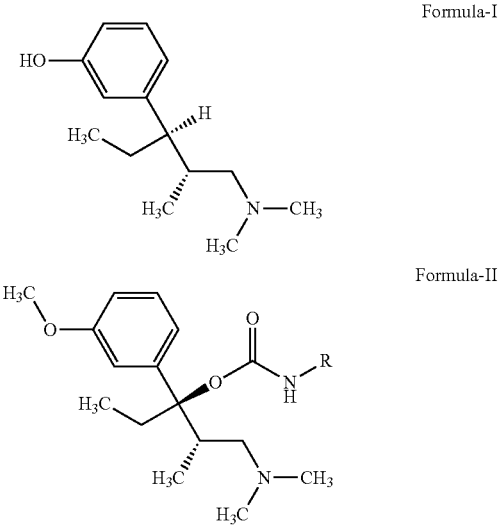

Formula-I

Formula-II

BACKGROUND OF THE INVENTION

3-[(1R,2R)-3-(Dimethylamino)-1-ethyl-2-methylpropyl] phenol is the IUPAC name for Tapentadol (Formula I). It is a centrally acting analgesic with a dual mode of action as an agonist of μ-opioid receptor and as a norepinephrine reuptake inhibitor.

U.S. Pat. No. 6,248,737 reissued as U.S. RE39593 discloses a variety of 1-phenyl-3-dimethylaminopropane compounds, processes for their preparation, pharmaceutical compositions comprising the compounds, and methods of use thereof. Among them, Tapentadol hydrochloride, is a one compound which has analgesic activity.

As per the process exemplified in U.S. RE39593 (hereinafter referred to as the '593 patent), (-)-(1R,2R)-3-(3-dimethylamino-1-ethyl-2-methylpropyl)-phenol hydrochloride is prepared by the reaction of (-)-(2S,3 S)-1-dimethylamino-3-(3-methoxyphenyl)-2-methylpentan-3-ol hydrochloride with thionyl chloride to produce (-)-(2S,3S)-[3-chloro-3-(3-methoxyphenyl)-2-methylpentyl]-dimethylamine hydrochloride; followed by subsequent removal of the chlorine substituent by treatment with zinc borohydride, zinc cyanoborohydride or tin cyanoborohydride, to produce (-)-(2R,3R)-[3-(3-methoxyphenyl)-2-methylpentyl]-dimethylamine hydrochloride; which is then converted into (-)-(1R,2R)-3-(3-dimethylamino-1-ethyl-2-methylpropyl) phenol hydrochloride by reaction with concentrated hydrobromic acid at reflux. Separation of the diastereoisomers, that is the two enantiomeric pairs, is carried out by precipitation of hydrochloride salt with trimethylchlorosilane/water in 2-butanone. The resolution of the racemic mixture of the two enantiomers of (2R,3R) and (2S,3S) configuration is carried by separation on a chiral HPLC column.

WO2004/108658 describes process for the preparation of (2R,3R)-3-(3-methoxyphenyl)-N,N,2-trimethylpentan-1-amine, the penultimate intermediate to prepare tapentadol, wherein the compound (2S,3S)-1-dimethylamino-3-(3-methoxyphenyl)-2-methylpentan-3-ol, is heated in acidic medium to get intermediate compound (Z,E)-(S)-[3-(3-methoxyphenyl)-2-methyl-pent-3-enyl]-dimethylamine HCl, which on catalytic hydrogenation yields enantiomeric mixture of (2R,3R)-3-(3-methoxyphenyl)-N,N,2-trimethylpentan-1-amine and (2R,3 S))-3-(3-methoxyphenyl)-N,N,2-trimethylpentan-1-amine. The required stereoisomer is separated to get (2R,3R)-3-(3-methoxyphenyl)-N,N,2-trimethylpentan-1-amine, which is treated with concentrated hydrobromic acid to get tapentadol.

WO2005/000788 describes another method of preparing tapentadol, wherein compound (2S,3S)-1-(dimethylamino)-3-(3-methoxyphenyl)-2-methyl-3-pentanol is subjected to dehydration reaction using heterogeneous catalyst to get intermediate compound (Z,E)-(S)-[3-(3-methoxyphenyl)-2-methyl-pent-3-enyl]-dimethyl amine hydrochloride, which on catalytic reduction yields enantiomeric mixture of (2R, 3R)-3-(3-methoxyphenyl)-N,N,2-trimethylpentan-1-amine and (2R,3 S))-3-(3-methoxyphenyl)-N,N,2-trimethylpentan-1-amine. The required stereoisomer is separated to get (2R,3R)-3-(3-methoxyphenyl)-N,N,2-trimethylpentan-1-amine.

WO2008/012046 describes another method for the preparation of tapentadol, wherein 1-(3-(benzyloxy)phenyl)propan-1-one is reacted with N-Methyl-N-methylene-methaneaminium chloride in presence of acetyl chloride and solvent acetonitrile to obtain compound 1-(3-(benzyloxy) phenyl)-3-(dimethylamino)-2-methylpropan-1-one. The compound is resolved with L-(-)-dibenzoyltartaric acid to get (S)-1-(3-(benzyloxy)phenyl)-3-(dimethylamino)-2-methylpropan-1-one. The isolated compound is then reacted with ethyl magnesium bromide undergoing Grignard reaction to isolate (2S,3R)-3-(3-(benzyloxy)phenyl)-1-(dimethylamino)-2-methylpentan-3-ol, which on reaction with trifluoroacetic anhydride in acetic acid results in acetylated compound. The acetylated compound on hydrogenolysis results in the compound 3-[(1R,2R)-3-(dimethylamino)-1-ethyl-2-methylpropyl]phenol of Formula-I.

WO2008012047 discloses a method for the preparation of tapentadol, wherein 1-(3-methoxyphenyl)propan-1-one is used as starting which converted to a hydroxyl intermediate compound (2S,3R)-1-(dimethylamino)-3-(3-methoxyphenyl)-2-methylpentan-3-ol through sequential reactions. Then this compound dehydrated to yield the compound (R)-3-(3-methoxyphenyl)-N,N,2-trimethylpent-3-en-1-amine, which after hydrogenation gives the mixture of compound (2R,3R))-3-(3-methoxyphenyl)-N,N,2-trimethylpentan-1-amine and (2R,3S)-3-(3-methoxyphenyl)-N,N,2-trimethylpentan-1-amine The required compound (2R,3R)-3-(3-methoxyphenyl)-N,N,2-trimethylpentan-1-amine is separated from the mixture by making hydrochloride salt. The isolated salt is dissolved in methane sulphonic acid and treated with methionine to get the compound 3-[(1R,2R)-3-(dimethylamino)-1-ethyl-2-methylpropyl]phenol, which is isolated as hydrochloride salt of tapentadol hydrochloride.

US20130137890 discloses preparation of tapentadol through the reaction of (S)-1-(dimethylamino)-2-methylpentan-3-one with 3-bromoanisole under Grignard conditions to get the compound (2S, 3R)-1-(dimethylamino)-3-(3-methoxyphenyl)-2-methyl-pentan-3-ol which convert into sulfonate esters followed by reductive deoxygenation to yield (2R,3R)-3-(3-methoxyphenyl)-N,N,2-trimethylpentan-1-amine and demethylation to obtain the compound 3-[(2R,3R)-1-(dimethylamino)-2-methylpentan-3-yl]phenol (tapentadol).

US20130096346 also discloses a preparation method of tapentadol through reacting an enantiomeric pair (2R,3R)/(2S,3S)-1-dimethylamino-3-(3-methoxyphenyl)-2-methyl-pentan-3-ol or an acid addition salt thereof with trifluoroacetic anhydride in a first solvent to produce a reaction mass, hydrogenating the reaction mass to produce an enantiomeric pair (2R,3R)/(2S,3S)-[3-(3-methoxyphenyl)-2-methylpentyl]-dimethylamine or an acid addition salt thereof, resolving the enantiomeric pair with a suitable optically active acid to produce an enantiomerically pure (-)-(2R,3R)-[3-(3-methoxyphenyl)-2-methylpentyl]-dimethylamine, demethylating the enantiomerically pure compound using a demethylating agent in a second solvent to produce tapentadol.

In spite of so many known processes, there is still need to have an efficient, economic and a safe process. The present inventors have found a novel process for preparation of 3-[(1R,2R)-3-(dimethylamino)-1-ethyl-2-methylpropyl]phenol, tapentadol of Formula I.

OBJECTIVE OF THE INVENTION

The objective of the invention is to provide a process for preparation of 3-[(1R,2R)-3-(dimethylamino)-1-ethyl-2-methylpropyl]phenol of Formula I or its pharmaceutically acceptable salt,

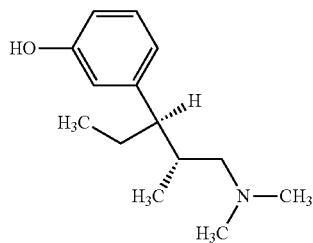

Formula-I wherein said novel process involves the use of a novel intermediate of Formula II

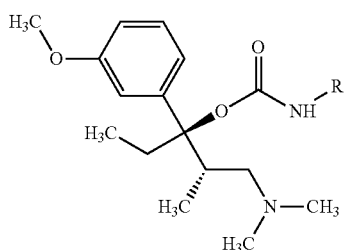

Formula-II wherein R is alkyl, cycloalkyl, aryl or substituted aryl.

SUMMARY OF THE INVENTION

The present invention provides A process for preparation of 3-[(1R,2R)-3-(dimethylamino)-1-ethyl-2-methylpropyl]phenol of Formula-I.

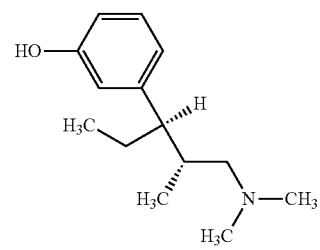

Formula-I and its pharmaceutically acceptable salts, wherein the process comprises:
a) reacting (2S,3R)-1-(dimethylamino)-3-(3-methoxyphenyl)-2-methylpentan-3-ol of Formula-III

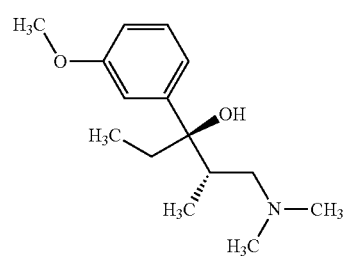

Formula-III with isocyanate of Formula-IV,

Formula-IV wherein R is alkyl, cycloalkyl or aryl, to give a compound of Formula II,

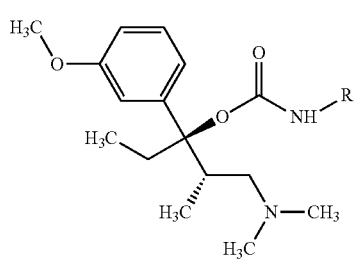

Formula-II b) hydrogenating the compound of Formula II to compound of Formula V,

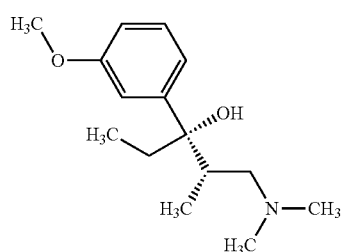

Formula-V c) subjecting the compound of Formula V to demethylation to give compound of Formula I,
d) optionally, converting the compound of Formula I to its pharmaceutically acceptable salts.

The present invention also provides a compound of Formula II or salts thereof,

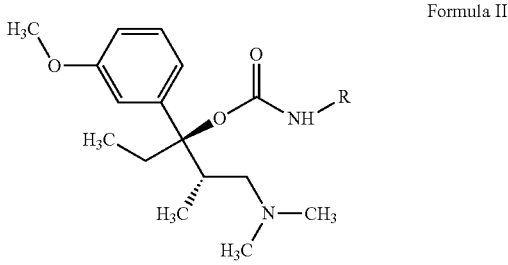

Formula II wherein R is alkyl, cycloalkyl, aryl or substituted aryl.

The present invention also provides a process for preparation of compound of Formula II or salts thereof,

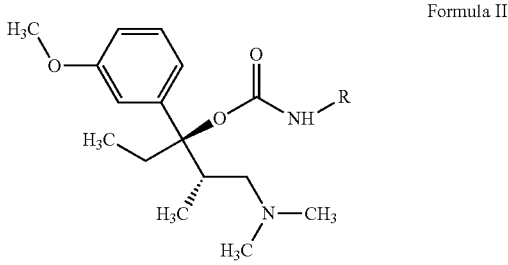

Formula II wherein R is alkyl, cycloalkyl or aryl comprising reacting (2S,3R)-1-(dimethyl amino)-3-(3-methoxyphenyl)-2-methylpentan-3-ol of Formula III

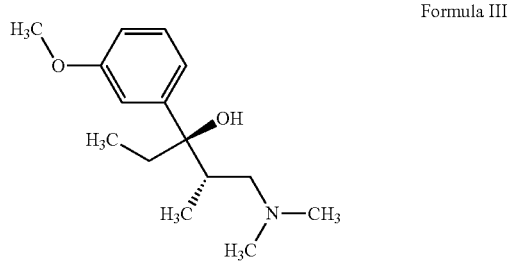

Formula III with isocynate of Formula IV,

Formula-IV and optionally, converting the compound of Formula II into its salt.

The details of one or more embodiments of the present invention are set forth in description below. Other features, objects and advantages of the invention will be apparent from the appended examples.

DESCRIPTION OF THE INVENTION

The general terms used hereinbefore and hereinafter preferably have within the context of this disclosure the following meanings, unless otherwise indicated.

The term "alkyl" refers to a hydrocarbon chain radical that includes solely carbon ($C_1$-$C_6$) and hydrogen atoms in the backbone, either linear or branched and which is attached to the rest of the molecule by a single bond, e.g., methyl, ethyl, n-propyl, 1-methylethyl (isopropyl), n-butyl, n-pentyl, and 1, 1-dimethylethyl (t-butyl).

The term "cycloalkyl" denotes a non-aromatic mono-, or multicyclic ring system of 3 to about 12 carbon atoms. Monocyclic rings include, but are not limited to cylcopropyl, cyclobutyl, cyclopentyl and cyclohexyl. Examples of simple multicyclic cycloalkyl groups include perhydronapththyl, perhydroindenyl etc; bridged multicyclic groups include adamantyl and norbornyl etc, and spriromulticyclic groups for e.g., spiro(4,4)non-2-yl. Unless set forth or recited to the contrary, all cycloalkyl groups described or claimed herein may be substituted or unsubstituted and may optionally contain one or more heteroatom selected from O, S and N.

The term "aryl" refers to an aromatic radical having 6 to 14 carbon atoms, including monocyclic, bicyclic and tricyclic aromatic systems such as phenyl, naphthyl, tetrahydronapthyl, indanyl and biphenyl. Unless set forth or recited to the contrary, all aryl groups described or claimed herein may be substituted or unsubstituted. The aryl moiety may be substituted or unsubstituted. Unless otherwise specified, the term "substituted" as used herein refers to a group or moiety having one or more of the substituents attached to the structural skeleton of the group or moiety, including, but not limited to such substituents as, nitro, alkyl, aryl, arylalkyl, cycloalkyl, cycloalkylalkyl, cycloalkenyl, heteroaryl, heterocyclylalkyl ring, heteroarylalkyl, heterocyclic ring.

In one aspect, the present invention provides a process for preparation of 3-[(1R,2R)-3-(dimethylamino)-1-ethyl-2-methylpropyl]phenol of Formula-I.

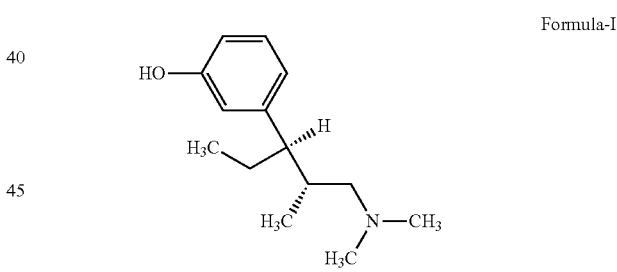

Formula-I and its pharmaceutically acceptable salts, wherein the process comprises:
a) reacting (2S,3R)-1-(dimethylamino)-3-(3-methoxyphenyl)-2-methylpentan-3-ol of Formula-III

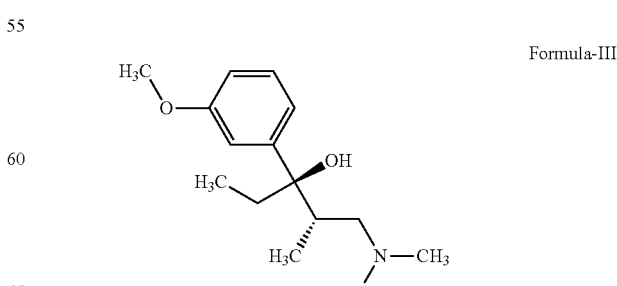

Formula-III with isocyanate of Formula-IV,

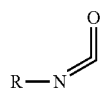

Formula-IV wherein R is alkyl, cycloalkyl or aryl, to give a compound of Formula II,

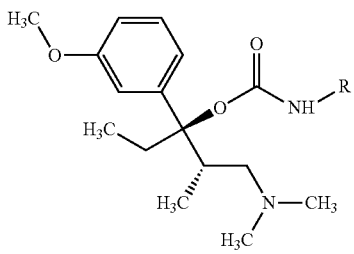

Formula-II b) hydrogenating the compound of Formula II to compound of Formula V,

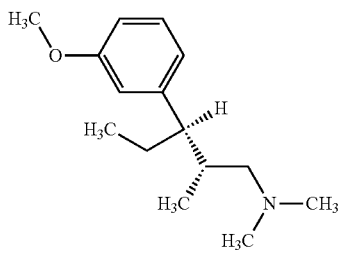

Formula-V c) subjecting the compound of Formula V to demethylation to give compound of Formula I,
d) optionally, converting the compound of Formula I to its pharmaceutically acceptable salts.

The compound (2S,3R)-1-(dimethylamino)-3-(3-methoxyphenyl)-2-methylpentane-3-ol of Formula III used as starting material for preparation of novel intermediate of Formula II can be obtained by the processes disclosed in prior art. For example, the compound of Formula III can be prepared by processes disclosed in U.S. Pat. No. 8,138,376 and US publication number 2010/0099916.

In step a) the compound of Formula III is treated with isocyanate of Formula IV, wherein R is alkyl, cycloalkyl, aryl or substituted aryl. Alkyl, cycloalkyl, aryl and substituted aryl groups are as defined above. As another embodiment of step a) the Formula III can be treated with Formula IV in presence of a suitable solvent. The suitable solvent may be selected from group comprising $C_1$-$C_4$ alcohols like methanol, ethanol, isopropyl alcohol, n-propanol, n-butanol, iso-butanol or tert-butanol etc., ethers like dioxane, tetrahydrofuran (THF), diethyl ether, methyl tert-butyl ether, diisopropyl ether etc., sulfoxides like dimethylsulfoxide etc., esters like ethyl acetate, ethyl butyrate, isopropyl acetate, methyl acetate, methyl propionate, propyl acetate, isoamyl acetate, isobutyl acetate, butyl acetate, sec-butyl acetate, tert-butyl acetate etc., halogenated solvents like carbon tetrachloride, chlorobenzene, chloroform, 1,1-dichloroethane, 1,2-dichloroethane, 1,1-dichloroethene, dichloromethane, 1,2-dichloroethene, 1,1,2,2-tetrachloroethane etc., hydrocarbons like benzene, toluene, xylene etc. and amides like dimethylacetamide, dimethylformamide, formamide, N-methyl-2-pyrrolidone, N-methylformamide, 2-pyrrolidone etc. A base may be added during the reaction for facilitate forward reaction. The base may be selected from a group of triethylamine, diethylamine etc. R in compound of Formula II is as defined above. Once the reaction is over, work-up is done to obtain compound of Formula II as free base. Free base of compound of Formula II can directly be taken into next step with or without isolating it from the reaction mass. As an embodiment of step 'a' the compound of Formula II can be converted into suitable acid addition salts by treating with suitable acid. Suitable acids include but are not limited to hydrochloric acid, hydrobromic acid, sulphuric acid, methanesulfonic acid, formic acid, acetic acid, oxalic acid, succinic acid, tartaric acid, mandelic acid, fumaric acid, lactic acid, citric acid, glutamic acid and aspartic acid. In a preferred embodiment, the acid addition salt is the citrate salt of Formula IIa, wherein R is as defined above.

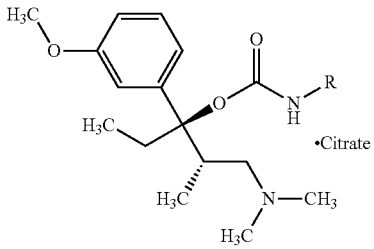

Formula IIa

In another embodiment R in compound of Formula IV and II is selected from phenyl, ethyl or cyclohexyl.

In another embodiment step 'a' the compound of Formula II is converted into its salt.

In step b), the compound of Formula II is converted into a compound of Formula V or salts thereof. As an embodiment of step b), the conversion is carried out by hydrogenolysis in presence of a catalyst and hydrogen gas. Hydrogenolysis can be performed in a suitable solvent like $C_1$-$C_4$ alcohols like methanol, ethanol, isopropyl alcohol, n-propanol, n-butanol, iso-butanol or tert-butanol etc., ethers like dioxane, tetrahydrofuran (THF), diethyl ether, methyl tert-butyl ether, diisopropyl ether etc., sulfoxides like dimethylsulfoxide etc., esters like ethyl acetate, ethyl butyrate, isopropyl acetate, methyl acetate, methyl propionate, propyl acetate, isoamyl acetate, isobutyl acetate, butyl acetate, sec-butyl acetate, tert-butyl acetate etc., halogenated solvents like carbon tetrachloride, chlorobenzene, chloroform, 1,1-dichloroethane, 1,2-dichloroethane, 1,1-dichloroethene, dichloromethane, 1,2-dichloroethene, 1,1,2,2-tetrachloroethane etc., hydrocarbons like benzene, toluene, xylene etc. and amides like dimethylacetamide, dimethylformamide, formamide, N-methyl-2-pyrrolidone, N-methylformamide, 2-pyrrolidone etc. Preferably, the solvent is THF.

In another embodiment step 'b' involves converting the salt of compound of Formula II to the compound of Formula V or salt thereof.

In another embodiment, the catalyst used for hydrogenolysis may be selected from the group comprising palladium, palladium on carbon, palladium on alumina, palladium salts like palladium chloride, palladium acetate, platinum, platinum on carbon, ruthenium on carbon and rhodium on carbon etc.

Compound of Formula V can be isolated as free base or as acid addition salts thereof. The acid addition salts can be as described in embodiments of step a). The preferred acid addition salt is hydrochloride.

In step c), the compound of Formula V or its acid addition salt is demethylated to afford compound of Formula I. As an embodiment of step c), demethylation is carried out using suitable reagents selected from the group consisting of iodotrimethylsilane, sodium ethyl sulphide, lithium iodide, methionine and hydrobromic acid, preferably hydrobromic acid. The reaction is carried out in appropriate solvent. The appropriate solvent may be selected form the group of water.

In step d), compound of Formula I can optionally be converted into its pharmaceutically acceptable salts via reaction with suitable acid in a manner well known to those skilled in the art. As an embodiment of step d), suitable acid may be selected from a group of hydrochloric acid, hydrobromic acid, sulphuric acid, methanesulfonic acid, formic acid, acetic acid, oxalic acid, succinic acid, tartaric acid, mandelic acid, fumaric acid, lactic acid, citric acid, glutamic acid and aspartic acid. In a preferred embodiment, the acid is the hydrochloric acid.

The complete process can be depicted as scheme provided below:

In another aspect, the present invention provides a compound of Formula II or salts thereof,

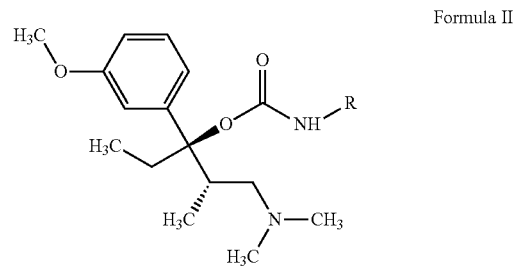

Formula II wherein R is $C_1$-$C_6$ alkyl, $C_3$-$C_{12}$ cycloalkyl or aryl.

As an embodiment of the aspect, salts of compound of Formula II can be acid addition salt with a suitable acid. Suitable acids include but are not limited to hydrochloric acid, hydrobromic acid, sulphuric acid, methanesulfonic acid, formic acid, acetic acid, oxalic acid, succinic acid, tartaric acid, mandelic acid, fumaric acid, lactic acid, citric acid, glutamic acid and aspartic acid. In a preferred embodiment, the acid addition salt is the citrate salt of Formula IIa.

None of the prior art disclosing process for preparation of tapentadol provides carbamates of compound of Formula II. Carbamate derivatives of Formula II provide unique advantage for preparation of tapentadol.

In another aspect, present invention provides a process for preparation of compound of Formula II,

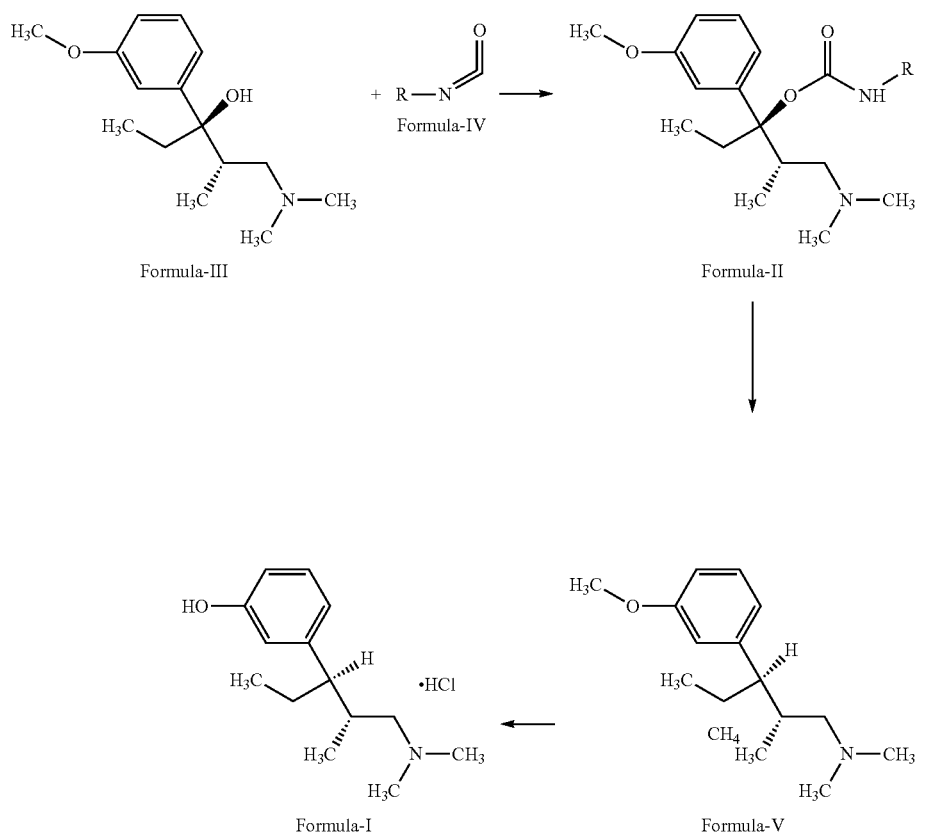

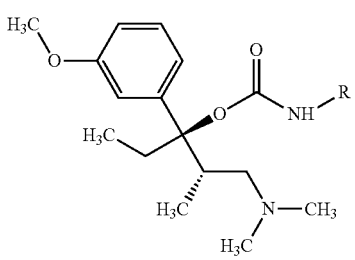

Formula II wherein R is alkyl, cycloalkyl or aryl comprising, reacting (2S,3R)-1-(dimethyl amino)-3-(3-methoxyphenyl)-2-methylpentan-3-ol of Formula III

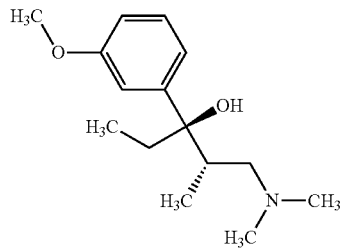

Formula III with isocynate of Formula IV,

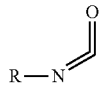

Formula IV wherein R is as defined above.

As an embodiment, compound of Formula II can optionally be converted into its salts as described under embodiment of first aspect.

Other embodiments of this aspect are same as embodiments of step a) of first aspect.

The present invention is further illustrated in detail with reference to the following example. It is desired that the example be considered in all respect as illustrative and are not intended to limit the scope of the claimed invention.

EXAMPLES

Example 1

Preparation of phenyl carbamic acid (1R,2S)-3-dimethylamino-1-ethyl-1-(3-methoxy phenyl)-2-methyl propyl ester citrate

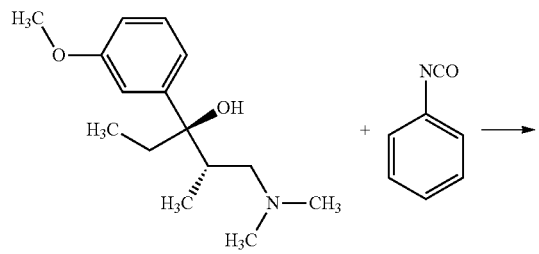

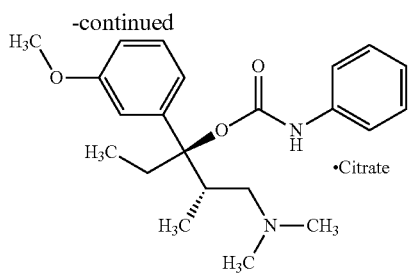

Method: 1

To a solution of the (2S,3R)-1-Dimethylamino-3-(3-methoxy phenyl)-2-methyl pentan-3-ol (50.0 g) in tetrahydrofuran (500 ml), phenyl isocyanate (32.6 ml) and triethyl amine (2.8 ml) are added and the mixture is heated at 70° C. for 5 hrs. After completion of reaction, reaction mixture is quenched with demineralized (DM) water (142 ml) at 45-50° C. and then stirred for 15-30 min at 25-30° C. Tetrahydrofuran is removed under reduced pressure at 40-45° C. Toluene (357 ml) and DM water (500 ml) are added to the residue and stirred at 25-30° C. for 1 hr followed by another 30 min at 0-5° C. Solid thus obtained is filtered. The filtrate is treated with anhydrous citric acid (36.5 g) and then stirred for 1 hr at 25-30° C. Aqueous layer is separated and washed with toluene (1×50 ml). The aqueous layer is concentrated under reduced pressure at 50° C. and traces of water is removed by stripping the residue with methanol (200 ml) under reduced pressure at 55° C. for 3-4 hrs, which is used in the next step without isolation/purification. HPLC purity—95.97%.

Method: 2

To a solution of the (2S,3R)-1-Dimethylamino-3-(3-methoxy phenyl)-2-methyl pentan-3-ol (170 g) [obtained from the reaction between ethyl magnesium bromide and (S)-3-(Dimethylamino-1-(3-methoxyophenyl-2-methylpropane-1-one (150 g)] in 2-methyl tetrahydrofuran (900 ml), phenyl isocyanate (111 ml) and triethyl amine (9.8 ml) are added and the mixture is heated at 80-90° C. for 5 hrs. After completion of reaction, reaction mixture is quenched with DM water (450 ml) at 45-50° C. and then stirred for 15-30 min at 25-30° C. 2-Methyl tetrahydrofuran is removed under reduced pressure at 40-45° C. Toluene (950 ml) and DM water (950 ml) are added to the residue and stirred at 25-30° C. for 1 hr followed by another 30 min at 0-5° C. Solid thus obtained is filtered; the filtrate is treated with anhydrous citric acid (124.8 g) and then stirred for 1 hr at 25-30° C. Aqueous layer is separated and washed with toluene (150 ml). The aqueous layer is concentrated under reduced pressure at 50° C. and traces of water is removed by stripping the residue with methanol (600 ml) under reduced pressure at 55° C. for 3-4 hrs, which is used in the next step without isolation/purification. HPLC purity—87.65%.

Example 2

Preparation of phenyl carbamic acid (1R,2S)-3-dimethylamino-1-ethyl-1-(3-methoxy phenyl)-2-methyl propyl ester citrate To a solution of (2S,3R)-1-Dimethylamino-3-(3-methoxy phenyl)-2-methyl pentan-3-ol (1.0 gm) in tetrahydrofuran (10 ml) at room temperature is added phenyl isocyanate (0.63 ml) and triethyl amine (0.055 ml). The resultant reaction mixture is refluxed at 75-78° C. for 4-5 hours. Reaction mixture is then allowed to cool to room temperature and quenched with DM water. (5 ml). The resultant mixture is then concentrated under reduced pressure at 45° C. Toluene (20 ml) and DM water (15 ml) are added to the residue, resultant heterogenous slurry stirred at 0-5° C. for 15-20 minutes and then the contents are filtered to remove unwanted solid residue. Citric acid (0.85 gm) is added to the filtrate and stirred at room temperature for 45 minutes. Organic and aqueous layers are separated and aqueous layer is concentrated under reduced pressure at 45° C. White floppy solid is obtained as citrate salt. 150 mg of this citrate salt is taken; DM water (10 ml) is added to it and basified with saturated sodium bicarbonate solution. Aqueous layer is extracted with ethyl acetate (2×15 ml) and combined ethyl acetate layer is dried over anhydrous sodium sulphate and concentrated under reduced pressure at 50° C. to get free base.

$^1$H-NMR (500 MHz, CDCl$_3$): 0.87 (t, J=7.25 Hz, 3H); 0.93 (d, J=6.90 Hz, 3H); 1.65-1.74 (br m merged with H$_2$O peak in CDCl$_3$, 2H); 2.16 (s, 6H); 2.35-2.40 (br d, 1H); 2.54 (sextet, J=7.25 Hz, 1H); 2.64 (sextet, J=7.35 Hz, 1H); 2.71-2.79 (m, 1H); 3.82 (s, 3H); 6.79-6.83 (m, 1H); 6.88-6.93 (br d, 2H); 7.06 (t, J=7.15 Hz, 1H); 7.24-7.33 (m merged with CDCl$_3$ peak, 3H); 7.41 (d, J=7.50 Hz, 2H).

Example 3

Preparation of (2R,3R)-[3-(3-methoxyphenyl)-2-methylpentyl]dimethylamine hydrochloride

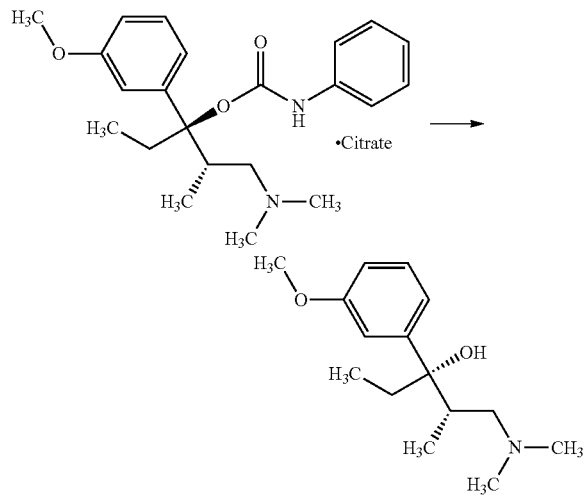

Phenyl carbamic acid (1R,2S)-3-dimethylamino-1-ethyl-1-(3-methoxy phenyl)-2-methyl propyl ester citrate (70 g) dissolved in tetrahydrofuran (420 ml) at 40-45° C. and treated with activated charcoal (1.4 g) at 40-45° C. for 20-30 min. The solution is filtered, filtrate is treated with Palladium (II) acetate (1.4 g) and activated charcoal (10 g) and then hydrogenolysis is carried out at 50-55° C. under 8-9 kg pressure of hydrogen in autoclave apparatus for 16-17 hrs. After completion of reaction, charcoal is filtered and washed with methanol (1×140 ml). Filtrate is concentrated under reduced pressure at 55° C., residue is dissolved in DM water (500 ml) and washed with ethyl acetate (1×210 ml). Aqueous layer is cooled to 10-15° C., made basic by addition of 25% aqueous sodium hydroxide (NaOH) solution (60 ml) to get pH-10-12 and then extracted with toluene (1×350 ml, 1×140 ml). Combined organic layer is washed with DM water (140 ml) and concentrated under reduced pressure at 50-55° C. The residual mass is dissolved in ethyl acetate (247 ml), concentrated hydrochloric acid (Conc. HCl) (15.3 ml) is added at 25-30° C. and stirred for 15 min. White solid thus obtained is filtered and washed with ethyl acetate (1×78 ml). Combined filtrate is concentrated under reduced pressure at 50° C. to get white solid. White solid is stirred with ethyl acetate (247 ml) at 60-65° C. for 30 min and then stirred at 0-5° C. for 1 hr. Solid product is filtered, washed with chilled ethyl acetate (1×30 ml, 1×20 ml) and dried at 50-55° C. Dry product (23.0 g) is dissolved in dichloromethane (100 ml) followed by slow addition of toluene (325 ml) and stirred for 2-3 h at 25-30° C. Solid thus obtained is filtered, washed with mixture (1x 17 ml) of dichloromethane: toluene (4:13) and dried at 50-55° C. HPLC purity—99.12%.

Example 4

Preparation of 3-[(1R,2R)-3-(dimethylamino)-1-ethyl-2-methylpropyl]phenol hydrochloride

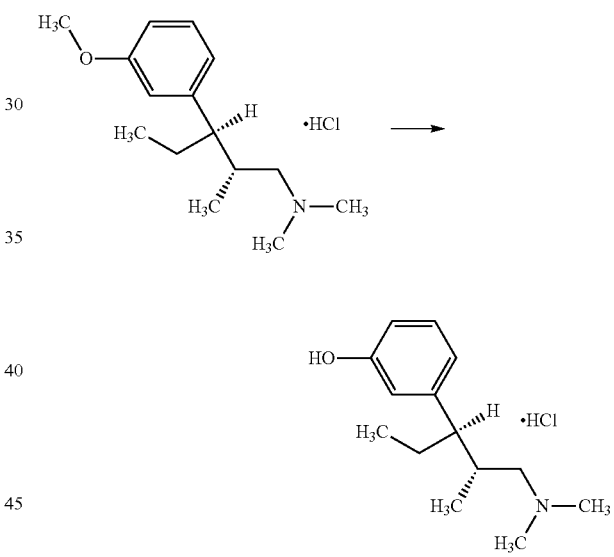

Aqueous hydrobromic acid (aq. HBr) (48%, 9 ml) is added to (2R,3R)-[3-(3-methoxy phenyl)-2-methyl pentyl] dimethylamine hydrochloride (3 g) and the resultant mixture is heated at 105-110° C. for 2 hrs. Reaction mixture is concentrated under reduced pressure at 65° C. DM water (15 ml) is added to the residue, made basic by addition of aqueous ammonia to get pH~10-11 and then extracted with ethyl acetate (2×15 ml). Combined organic layer is washed with DM water (1×5 ml) and concentrated under reduced pressure at 60° C. Residue is dissolved in isopropanol (IPA) (12.5 ml), IPA-HCl (3 ml) is added to it and stirred at 25-30° C. for 1 hr. Solid thus obtained is filtered, washed with isopropanol (2×2.5 ml) and dried at 50-55° C. for 16-17 h in air oven. HPLC purity—99.4%, Chiral purity—100%.

The process disclosed in examples can also be used to prepare compound of Formula II with R as ethyl and cyclohexyl by using ethylisocyanate and cyclohexylisocyanate, respectively.

The invention claimed is:

1. A process for preparation of 3-[(1R,2R)-3-(dimethylamino)-1-ethyl-2-methylpropyl]phenol of Formula-I

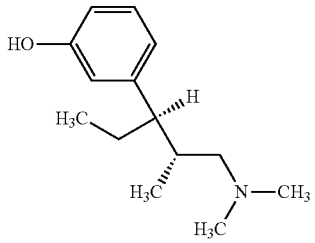

Formula-I and its pharmaceutically acceptable salts, wherein the process comprises:

a) reacting (2S,3R)-1-(dimethylamino)-3-(3-methoxyphenyl)-2-methylpentan-3-ol of Formula-III

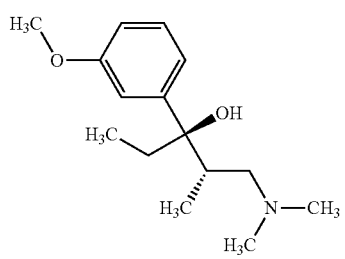

Formula-III with isocyanate of Formula-IV,

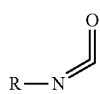

Formula IV wherein R is selected from $C_1$-$C_6$ alkyl, $C_3$-$C_{12}$ cycloalkyl or aryl, to give a compound of Formula II,

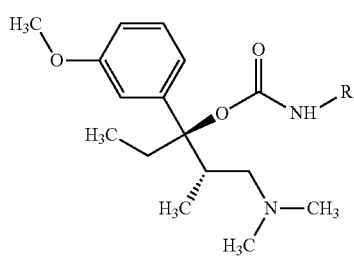

Formula-II b) hydrogenating the compound of Formula II to compound of Formula V,

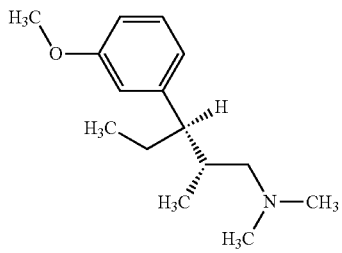

Formula-V c) subjecting the compound of Formula V to demethylation to give compound of Formula I, d) optionally, converting the compound of Formula I to its pharmaceutically acceptable salts.

2. The process as in claim 1 wherein R in compound of Formula IV and II is selected from phenyl, ethyl or cyclohexyl.

3. The process as in claim 1 wherein step a carried out in presence of a base.

4. The process as in claim 1, wherein in step 'a' the compound of Formula II is converted into its salt.

5. The process as in claim 1, wherein step 'b' involves converting the salt of compound of Formula II to the compound of Formula V or salt thereof.

6. A compound of Formula II or salts thereof,

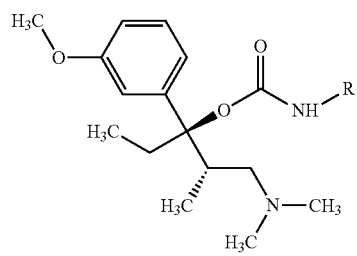

Formula II wherein R is $C_1$-$C_6$ alkyl, $C_3$-$C_{12}$ cycloalkyl or aryl.

7. The compound as in claim 6 wherein R is selected from phenyl, ethyl or cyclohexyl.

8. The compound of claim 6 wherein the salt is citrate or hydrochloride.

9. A process for preparation of compound of Formula II or salts thereof,

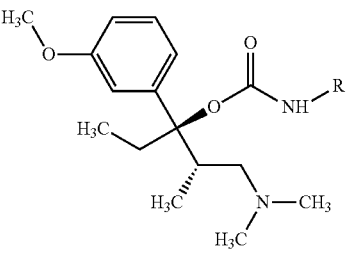

Formula II wherein R is $C_1$-$C_6$ alkyl, $C_3$-$C_{12}$ cycloalkyl or aryl comprising reacting (2S,3R)-1-(dimethyl amino)-3-(3-methoxyphenyl)-2-methylpentan-3-ol of Formula III with isocynate of Formula IV,
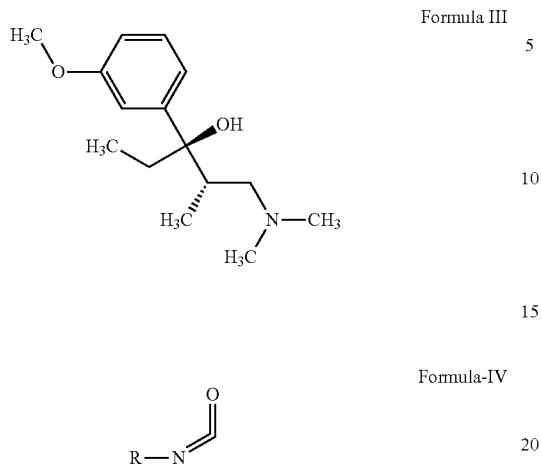
Formula III
Formula-IV
and optionally, converting the compound of Formula II into its salt.
10. The process as in claim 9 wherein R is selected from phenyl, ethyl or cyclohexyl.
* * * * *